United States Patent [19]
Acquaire

[11] Patent Number: 6,059,777
[45] Date of Patent: May 9, 2000

[54] METHOD AND PROCESS FOR NON-INVASIVE SUB-EPIDERMAL PERMANENT HAIR REMOVAL

[76] Inventor: Florence Acquaire, 9 Post Rd., Oakland, N.J. 07436

[21] Appl. No.: 09/003,683

[22] Filed: Jan. 7, 1998

[51] Int. Cl.[7] .................................................. A61B 17/50
[52] U.S. Cl. ................................................................ 606/13
[58] Field of Search .................................. 606/131, 133, 606/36, 43

[56] References Cited

U.S. PATENT DOCUMENTS 4,940,466  7/1990  Paduano et al. ........................... 606/36

FOREIGN PATENT DOCUMENTS

2143739  2/1985  United Kingdom .

*Primary Examiner*—Michael Buiz
*Assistant Examiner*—Vy Q. Bui
*Attorney, Agent, or Firm*—Ward & Olivo

[57] ABSTRACT

The present invention relates to a method for permanently removing hair from an area of patient's skin through non-invasive nor damaging system and process. The method of the present invention is non-invasive whereby the needle/probe is only inserted into a portion of the hair follicle, and never exceeding its confines. The present invention provides an improved epilation system for permanent removal of hair which relies upon finite and specific steps for non-invasive, safe, non-damaging, permanent hair removal with optimal effectiveness and with minimal or no patient discomfort; accomplishing ablation of not only the hair, but it's root structure and more importantly the specific capillary network that supports the hairs growth. Additionally, the present disclosure is highly cost effective to the patient due to short term treatment or singular treatment per hair. Accordingly, the present invention is designed to provide an improved epilation system for permanent removal of hair which relies upon finite and specific steps for non-invasive, safe, non-damaging, cost effective, permanent hair removal with optimal effectiveness and with minimal or no patient discomfort so as to ablate only the hair, it's root structure and vascular system which supports the growth of the hair.

7 Claims, 5 Drawing Sheets

METHOD AND PROCESS FOR NON-INVASIVE SUB-EPIDERMAL PERMANENT HAIR REMOVAL

BACKGROUND OF THE INVENTION

The present invention relates to a non-invasive system for sub-epidermal epilation and permanent hair removal from sub-epidermal tissue (Sub-Epidermal-System "SES"), and particularly to an improved system and method for hair removal utilizing high frequency induced cellular coagulation within the hair follicle. Unwanted hair is a common dermatological and cosmetic problem, and can be caused by heredity, malignancy, or endocrinologic diseases such as hypertrichosis (i.e., excess hair), hirsutism (i.e., androgen-influenced hair) as well as prior attempts at follicular hair removal that only further stimulates hair growth.

Growth of each hair is originated by germinativa fibroblast cells in the basal layer of the epidermis. The hair grows both outwards and inwards during its growth cycle, and the follicle develops as an encapsulating pouch extending beyond the epidermis and down several millimeters in depth to the dermis and in the rare case bridges on the subcutaneous fat. Hair remains attached to the base of the follicle, where a capillary network develops to provide nourishment. During the anagenic growth phase, hair matrix cells divide rapidly and migrate upwards to form the shaft. A subsequent catagenic phase is marked by cessation of mitosis, and the reabsorption of the lower part of the follicle. Capillary nourishment is greatly reduced during this phase. In this or the final telogenic (resting) phase, the hair falls out and a new hair may replace it in a new growth cycle. At any particular time, approximately 10% of scalp hairs will be in telogenic mode.

The growth cycle varies with anatomical location from as little as three (3) months for facial hair to as much as seven (7) years on the scalp. However, hair in high friction and pubic areas may be retained by the body as protection and may not shed at all.

The hair follicle consists of a mixture of germinativa cells and melanocytes. Sebaceous cells empty into the follicle, providing a lipid-rich environment. The follicle may range between 0.1 and 0.001 mm in diameter and may extend to 4 mm in depth. The average hair diameter within the follicle is 0.125 mm. Hair itself is generated as an accumulation of dead (keratinized) cells. Structurally it consists of two (2) or three (3) discrete layers. The outer cuticle layer consists of a single layer of overlapping flap, acting as a protective barrier. In turn, an inner cortex layer may consist of any pigment which may be present (pigment may also reside in melanocytes lining the follicle). Pigment may exist as two melanin forms. Eumelanin is responsible for brown/black coloration and pheomelanin is responsible for red/blonde coloration. Larger, fully developed terminal hairs also contain a core known as the medulla.

In the lower follicular region, a bulge is formed where the arrector pili muscle contacts the follicle. This muscle controls movement and orientation of the hair and may, under appropriate stimuli, render the hair vertical with respect to the skin surface. The bulge area has one of the fastest rates of cell division found in mammals, stimulated by growth factors from the lower papilla area.

Finally, there is the bulb at the base of the hair follicle. Generally, the bulb area is the area in which the hair is initially generated and further attached to the body and nourished via predisposed capillaries.

While the hair follicle and hair contained therein function at several different levels, excess body hair does present a cosmetic problem for females and males. As a consequence, many individuals undergo hair removal treatments. Hair can be temporally removed using a number of techniques including wax removal, depilatory creams, lasers, and of course, shaving. Alternatively, in past electrolysis techniques hair may have been temporarily removed. These past applications of electrolysis techniques involved the intention of inserting a needle into a hair follicle capable of conducting electrical current, lye decomposition or both. The insertion and application of electrical current in turn has resulted in cellular destruction (scarring) that is often painful, with inefficient results, that in turn is time consuming because of the lack of specific needle placement in the subepidermal tissue, depths of insertion, heat application and duration of application.

Electrolysis is used by in excess of 1 million women in the United States. It is well known that in past and present techniques hair is temporarily remove by electrolysis wherein a needle/probe is inserted through the epidermis, hair follicle and dermis into the sub-cutaneous tissue, and beyond, well into the patient and well beyond the hair follicle. Then high voltage is applied as to a needle/probe generating heat when conducted in the body, thus destroying the surrounding cells, intended or otherwise. Such misdirected cellular destruction can result in dimpling and scarring. The primary problems with the prior techniques is in scarring and the creation of considerable pain caused by improper insertion of the needle/probe and application of high heat into the tissue of the patient.

Hair removal through electrolysis has been performed for many years, and through electrolysis, patients have been temporarily able to selectively remove hair from certain body areas. Ordinarily, this hair removal process is carried out by inserting a needle/probe into an individual's individual hair follicle and beyond. This obviously can be a very painful ordeal and also is unduly time consuming, because only one hair is removed at a time and may necessitate several applications, over the course of years, without permanency. In some techniques patients are grounded by having the patient hold a ground terminal in his/her hand. This results in electricity passing through a large area of the patient's body, which in some cases can cause efficiency and conductivity problems and can further destroy necessary tissue. In past electrolysis techniques, repeat treatment sessions over years are necessary to remove all unwanted hairs from a particular area, all without permanency and causing cellular damage.

In the early stages of electrolysis, there was much confusion and speculation as to why it worked. Some investigators, for example, postulated that the hair follicle was "electrocuted". Later, it was hypothesized that it works because of electrolytic action that gives rise to chemical decomposition in the hair follicle, but needless to say there was adverse chemical decomposition in surrounding cells.

Past electrolysis techniques, save the teachings herein, are still not well understood. Within each hair follicle, there is a solution of salt water that provides the chemicals for the electrolysis process to work. Specifically, subjecting the salt water solution to an electric current results in the salt (NaCl) and the water (H2O) breaking into their constituent chemical elements. This application is referred to as electrolysis, and the subsequent rearrangement of the basic elements of salt and water is referred to as ionization. One of the new compounds that is formed as a result of the ionization is sodium hydroxide (NaOH). The sodium hydroxide produced is highly caustic to the hair follicle and causes the follicle to die through a decomposition of the hair root, and inadvertent decomposition of the surrounding cellular structures. In some instances, by chance or luck, the general epithelium of the follicle is killed, rendering the follicle unable to ever produce more hair so long as the deadening reduces the capillary blood flow to the follicle, thus eliminating the possibility of cellular regeneration. After the hair follicle has been treated in this manner (decomposed), the hair can be removed by extraction without guarantee of permanency.

As shown in the patent to Cole (U.S. Pat. No. 5,026,369, hereinafter the "'369 patent"), the method of electrolysis may utilize an electrode solution as a medium for conducting current to the tissue and salt water content of the hair follicles. The electrode solution enhances conductivity because the skin surface and the hairs themselves are less effective conductors of electricity than is the electrode solution.

In the past, two techniques have been primarily used in the electrolysis field. Galvanic (DC) current can be passed down a fine needle/probe or needles inserted into the follicle. Tissue in the area of the electrical charge is converted from local tissue saline to sodium hydroxide, which destroys the follicle. Furthermore, the thermolysis technique utilizes an AC current to directly heat and thereby destroy the papilla. Some clinicians utilize a combination approach of these two electrolysis techniques. Some electrolysis techniques treat a single follicle at a time, in a painful procedure which can require localization or even anesthesia. Needle/probes are re-used in this unsanitary, non-permanent, time consuming, multiple treatment technique.

As pointed out above, hair removal through a conventional electrolysis technique, where the skin is actually perforated and then penetrated with a tapered, one-piece, inflexible needle/probe, is very painful. Therefore, a need exists for a painless and more efficient method for removing unwanted hair. Furthermore, most present day electrologists are self taught or have minimal formal training and therefore have minimal awareness of the finite demands associated with electrolysis and therefore may tend to harm rather than help the patient. Previous attempts to address the problems inherent with current and past techniques resulted in attempts to develop non-invasive electrolysis without substantive success.

In 1993, Thermotrex Corporation was assigned two Hair Removal Device and Method patents (U.S. Pat. Nos. 5,226, 907 and 5,425,728) based on the use of an externally applied chromophore to enhance local absorption of laser light. In these patents, a topically applied substance is said to penetrate to the full depth of the root of the follicle. The substances cited include permanent hair dyes, suspensions of carbon particles and photosensitizing compounds. A subsequent application of laser light is said to induce a photothermal reaction which destroys the follicle and a surrounding tissue area.

The compounds cited by Thermotrex in their patents will probably demonstrate follicular selectivity. Many other topical compounds, and some systemic compounds, exist as candidates. Liposomal or lipophilic compounds may favor the lipid rich environment. Alternatively, solvents such as ethanol may be used to de-lipidize or re-organize the sebum, and thereby open the follicular passageways. Deposition of hydrophilic drugs may be facilitated by the action of wetting agents such as sodium lauryl sulfate, which may promote the creation of an emulsion. Particle size clearly plays a role in terms of ability to penetrate through narrow epidermal structures and along the follicular duct. The approach cited in this invention may work, although its practice involves the use of expensive laser equipment. Further, the use of topical compounds prolongs treatment and raises potential risk without guarantee of success.

A second technique has been studied and reported by Drs. Melanie Grossman and Rox Anderson whereby single high energy normal mode Ruby laser pulses are applied to the skin in the absence of an externally applied chromophore. No issued patent has been awarded covering this work. In this method, the optical target is the melanin within the inner cortex layer and the pigment-bearing melanocytes lining the follicle. High frequencies of up to 60 J/sq.cm. are utilized in large spotsizes, with short pulse widths of the order of 150 mu sec and a wavelength of 694 nm. This technique employs a number of natural phenomena to enhance effect on the deep follicular component. A large applied spotsize and high fluence allow for maximum depth of penetration. Concurrent cooling spares bulk tissue structures from the edema and general damage which can result from the use of frequencies of this magnitude. Intimate index-matched contact of the custom handpiece with the tissue minimizes reflection loss. However, the short pulse widths used in this approach are unlikely to efficiently transfer heat to the entire follicular structure. The Ruby laser is not readily capable of the requisite millisecond-domain pulses necessary to effect a true thermal mechanism.

A third approach, utilizing the Q-Switched Ruby laser, was disclosed by Nardo Zaias in his 1990 U.S. Pat. No. 5,059,192. This patent cited the use of a Q-Switched Ruby laser at 694 nm, with 3–8 mm spotsize and around 8 J/sq.cm. Pulse width was in the range 30–40 nanoseconds. Light energy administered in such a short pulse width will be well retained in the melanocytes lining the follicle. This approach will provide potential for melanocyte destruction and perhaps permanent depigmentation or destruction of the hair, but likely will not kill the follicle itself, since the pulse width is insufficiently long to conduct heat away from the targeted melanin granules.

In 1967, U.S. Pat. No. 3,538,919 was filed by R. Meyer. Meyer cited the placement of a fiber directly into the follicle into which a total of 30–40 J/cm<2> of light was subsequently launched. This fluence was administered over a period of 1–2 milliseconds, preferably by a normal mode Ruby or Nd:YAG laser. Use of a 50 um fiber was cited. This fiber diameter would theoretically fit into a 100 urn follicle containing a 50 um hair, but with difficulty.

In 1970, Richard Harte filed U.S. Pat. No. 3,693,623, which also cited the placement of a fiber directly into each follicle to be destroyed. The light source here was a xenon lamp, which applied up to 3 mJ to each follicle, in an interval of less than 3 msec. This technique is a difficult process to administer.

In 1973, Carol Block was issued U.S. Pat. No. 3,834,391, which similarly addressed the placement of a fiber at the follicular entrance. Light source was unspecified. This patent introduced the concept of the use of mineral oil, said to facilitate light conduction, presumably by index matching. No additional chromophore was added.

In 1981, H. Weissman filed an application, later granted as U.S. Pat. No. 4,388,924. This cited the devitalization of hair by the specific destruction of the papillary blood supply. A narrow beam from an Argon laser was directed onto the tissue. This light was said to be absorbed by the papillary plexus, causing heating and coagulation. Multiple 20–30 millisecond exposures from a 0.5–2.5 Watt beam were cited. The hair was subsequently tweezed from its follicle. This method calls for the selective destruction of the papillary plexus and is unlikely to be practical using a narrow beam Argon laser, with its limited penetration depth capabilities, since this supply resides at several millimeter depth and is shielded by the overlying follicular structure. Indeed, no vascular specific lasers are likely to exhibit adequate dermal penetration.

In 1984, A. Sutton filed a patent, later granted as U.S. Pat. No. 4,617,926. This provided for the use of a fiber without a core, into which an individual hair slides by 2–3 mm, completing the wave guiding action. Different probes were cited, and about 1 Joule of energy launched into the fiber, from an unspecified laser source. In an alternative embodiment, the fiber is sharpened and inserted directly into the follicle. This technique is likely to result in rapid probe destruction. In Sutton it is alleged that the hair can be used as a optical waveguide to conduct the optical energy to the base of the follicle without damaging the surrounding tissues. No explanation is given as to how hair, which is not transparent nor hollow, can function as a waveguide, so that the operability of the Sutton proposal is questionable. Other proposals have involved probes which must be inserted much like electrolysis needle/probes to deliver the optical energy directly to the hair root. See Block U.S. Pat. No. 3,834,391 issued Sep. 10, 1974 and Mayer, U.S. Pat. No. 3,538,919 issued Nov. 10, 1970.

The delivery of the energy may be through the use of a hand piece having means for scanning a beam in order to locate the entrance to the hair root structure at the skin. Other automatic and semiautomatic systems for locating a housing carrying the laser beam and its optical system may be used. The U.S. patent to Weissman referenced above shows one such system.

Optical beams for hair removal have been suggested in several patents. Optical-based methods, such as the use of laser light, have also been used for hair removal. U.S. Pat. No. 4,388,924, for example, describes irradiation of individual hair follicles using a laser; in this method, heating of the hair's root section causes coagulation in local blood vessels, resulting in removal of the follicle. Related techniques, such as those described in U.S. Pat. No. 5,226,907, involve removal of the follicle by first applying a light-absorbing substance to the region of interest, and then irradiating the substance to heat and remove the follicle. The optical energy is not used to ablate the hair and its root structure as provided for by the present invention, in that beam delivery system is not an optical system which shapes and restricts the beam to a subcutaneous ablation cavity, that is a volume where ablation can occur and is restricted.

In U.S. Pat. No. 5,059,192, issued to Zaias and in a patent issued Jul. 13, 1993 to Tankovich, U.S. Pat. No. 5,226,907, reliance is placed on selective photo thermolysis, that is the selective absorption of the incident laser radiation by the melanin in the follicle to cause localized heating.

Like past electrolysis techniques, lasers also have proven limitedly effective in the permanent removal of hair, without regard to unnecessary scaring and cellular destruction. Previous attempts to address the problems inherent with temporary, un-safe, invasive, discomfiting hair removal have been ineffective and misdirected. The present invention provides for and teaches non-invasive, safe, non-damaging, permanent hair removal with optimal effectiveness and with minimal or no patient discomfort.

SUMMARY OF THE INVENTION

The present invention is designed to provide an improved epilation system for permanent removal of hair which relies upon finite and specific steps for non-invasive, safe, non-damaging, permanent hair removal with optimal effectiveness and with minimal or no patient discomfort so as to ablate only the hair, it's root structure and vascular system which supports the growth of the hair. Additionally, the present disclosure is highly cost effective to the patient over the long term.

Accordingly, the invention relates to a non-invasive system for eliminating hair from a localized area of skin. The process disclosed herein is non-invasive in that it does not entail penetrating the patient's epidermal tissue with a needle/probe or the like. Rather the epilator's needle/probe is partially inserted into the area of the hair follicle without perforating the side walls nor base (bulb) of the follicle. Thus, the present system is efficiently effective in it ability to permanently remove hair without the negative side effects nor consequences of prior techniques.

Disclosed herein is a guaranteed system and process for removal of unwanted hair comprising the general steps of: patient, hair and follicular assessment; bodily placement and positioning; epilator apparatus activation and adjustment; needle/probe insertion with proper depth maintenance; electrical current emitter with resulting low heat for cell coagulation; needle/probe removal; hair removal; repeated steps for area hair removal; patient re-assessment; patient self post "operative" treatment and possible "in-house" post "operative" treatment or visit. As will be evidenced with greater specificity in the ensuing sections, the present invention disclosed a system for particular needle/probe depth insertion coupled with proper electrical intensity as never before envisioned not practiced. The results as previously discussed herein are unmatched in scope and effectiveness. The present invention is designed to provide an improved epilation system for permanent removal of hair which relies upon finite and specific steps for non-invasive, safe, non-damaging, permanent hair removal with optimal effectiveness and with minimal or no patient discomfort so as to ablate only the hair, it's root structure and vascular system which supports the growth of the hair. Additionally, the present disclosure is highly cost effective to the patient over the long term.

Accordingly, objects of the invention include but are not limited to:

allowing for permanent hair removal while sparing the surrounding skin layers (e.g., the dermis and epidermis) from injury;

providing an electrical epilatory device in which no probes perforate the tissue of the patient;

providing an electrolysis method that is non-invasive in that the patient's skin is not penetrated by a needle/probe;

providing for finite and specific steps for non-invasive permanent hair removal;

providing an safe and efficient system for permanent hair removal;

providing a system that reduces or eliminates patient discomfort;

providing for a system that ablates only the hair, it's root structure and vascular system and not the surrounding cells;

providing for a system that uses low heat;

providing for a system that coagulates the hair follicle;

providing for a system that eliminates cellular regrowth or regeneration of the coagulated cells, and providing for a cost effective system for permanent hair removal.

Other objects and advantages of the present invention will become apparent and obvious from a study of the following description and the accompanying drawings, which are merely illustrative of the invention.

DETAILED DESCRIPTION OF THE INVENTION

The present invention relates to a system whereby low heat is controlled, balanced and exacted in the dermis. Thus, the hair follicle tissue is diminished and the protein coagulated retarding and eliminating additional and future regrowth of the hair follicle and the hair producing cells.

Accordingly, the steps are as follows:

A patient enters the electrologist's or doctor's office and fills out a medical history and/or insurance card, if applicable. The electrologist reviews the information and instructs the patient of the procedure, following which if the patient has questions or comments the same are responded to. Next, the patient is brought into the treatment room and body positioned in accordance with the area that is to be treated. Then the particular bodily part is placed in a manner to allow for treatment, and in certain instances the bodily part or extremity may be partially or totally immobilized. The electrologist or doctor then assess the hair follicle's opening and chooses the correct needle/probe and needle/probe diameter for insertion. The needle/probe is then prepared, in this application a non-tapered (straight needle), flexible needle/probe is used. Then the electrologist or doctor would turn on the epilator and set the intensity. Generally, the intensity for electrical current, as taught in this application, should be set at 1.75. Then the needle/probe is then inserted to a predetermined depth for a predetermined duration. Upon insertion the needle/probe is maintained in position and the epilator engaged such that the epilator emits a low level electrical current that slowly coagulates the hair follicle and surrounding cellular material. Thus, the coagulation effectively eliminates hair regrowth by eliminating the body's ability to supply the requisite blood supply the follicle and hair. The needle/probe is then removed and forceps are used to gently remove the hair from the coagulated hair follicle. Alternatively, if the hair does not "come out" easily, the needle/probe should be reinserted and electrical current reapplied to further coagulate the effected hair follicle, such that the hair can be removed without force. The hair is then disposed of and a new subject hair and hair follicle located. After the selected hair follicles are treated the patient is instructed in post "operative" treatments and if necessary additional possible "in-house" post "operative" treatment or visit may follow such as the use of tea tree oil.

Figure 1:
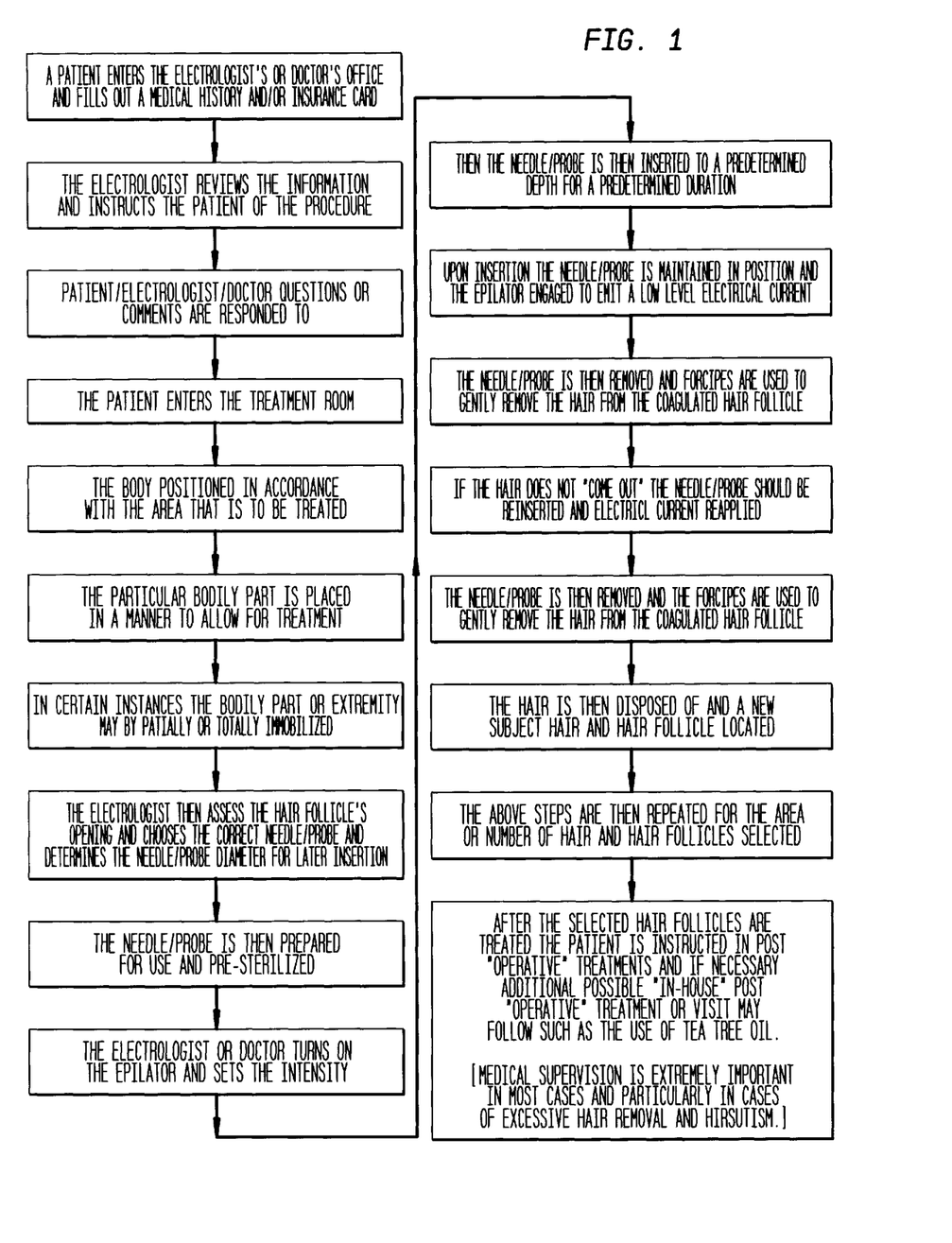
FIG. 1. Depicts an representational flow chart of the steps involved in the present disclosure.

FIG. 1 represents a flow chart of the steps involved in the present disclosure.

Figure 2:
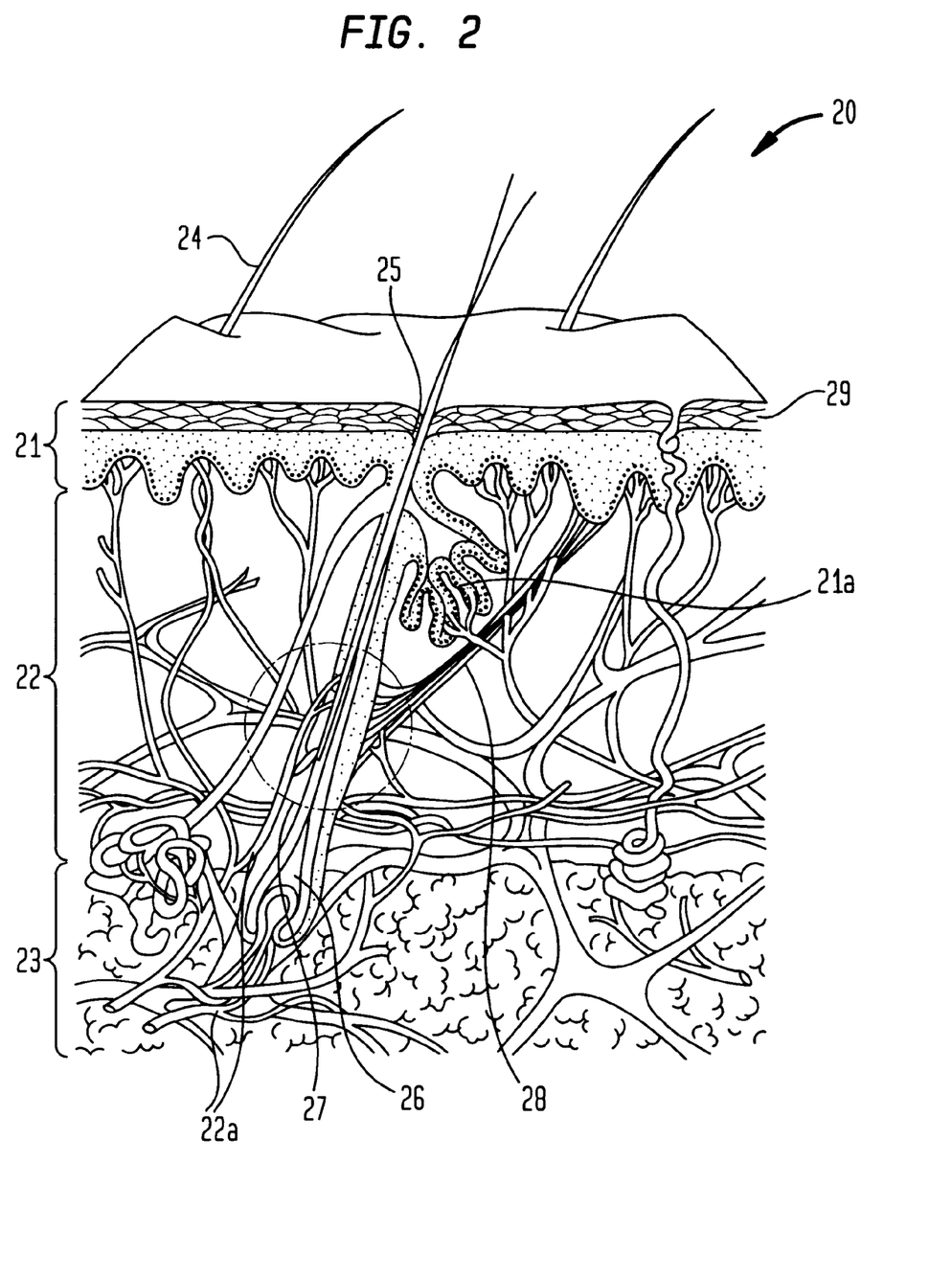
FIG. 2. Depicts a representational cross section of human skin.

FIG. 2 depicts a representational cross section of human skin 20 wherein the skin 20 for purpose of this diagram is comprised of an outer layer 29, epidermal 21 layer, dermal layer 22 and sebaceous layer 23. The hair 24 passes through the outer layer 29, epidermal layer 21 and into the dermal layer 22 via an opening and pouch area in the skin identified as the hair follicle 25. The hair follicle 25, extends through the outer layer 29, epidermal 21 layer, dermal layer 22 and sebaceous layer 23 to where the bulb 26 of the hair follicle is located. In turn, the bulge of the hair follicle 27 is located in the dermal 22 layer and is attached to the epidermis 21 via the erector plie muscle 28. Also locate in the dermal 22 layer is the sebaceous gland 21a. Throughout the epidermis 21, dermis 22 and subcutaneous 23 layers is a vascular system (demonstratively shown as 22a) that supply blood flow to the surrounding cells and hair follicle 25.

Figure 3:
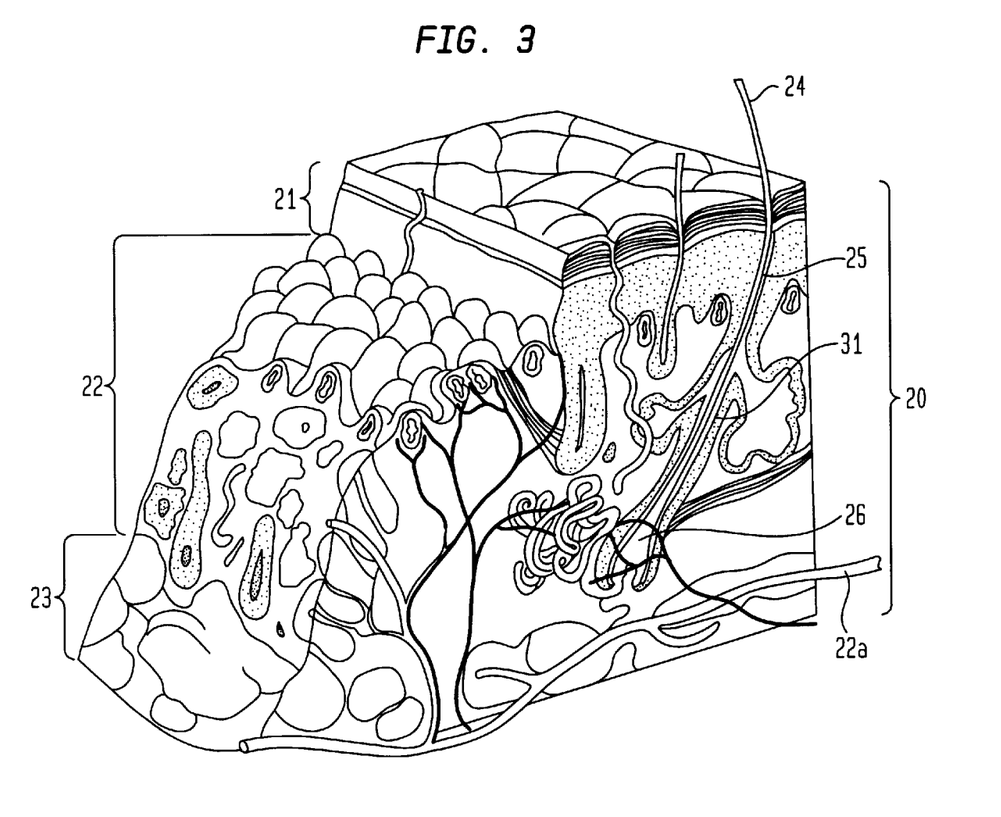
FIG. 3. Depicts a representational cross section of human skin.

FIG. 3 is a representational cross section of human skin. The skin 20 is comprised, for purpose of this disclosure of three layers: the epidermis 21, dermis 22 and subcutaneous 23 layer. Passing therethrough is the hair 24. The hair 24 passes through the aforementioned layers 21, 22, 23 via a fair follicle 25. The hair follicle 25 is comprised in part of a bulb 26 that received blood from blood vessels 22a. The blood vessels 22a also feed the shaft 31 of the hair follicle 25 with nutrients all of which promotes hair 24 growth.

Figure 4:
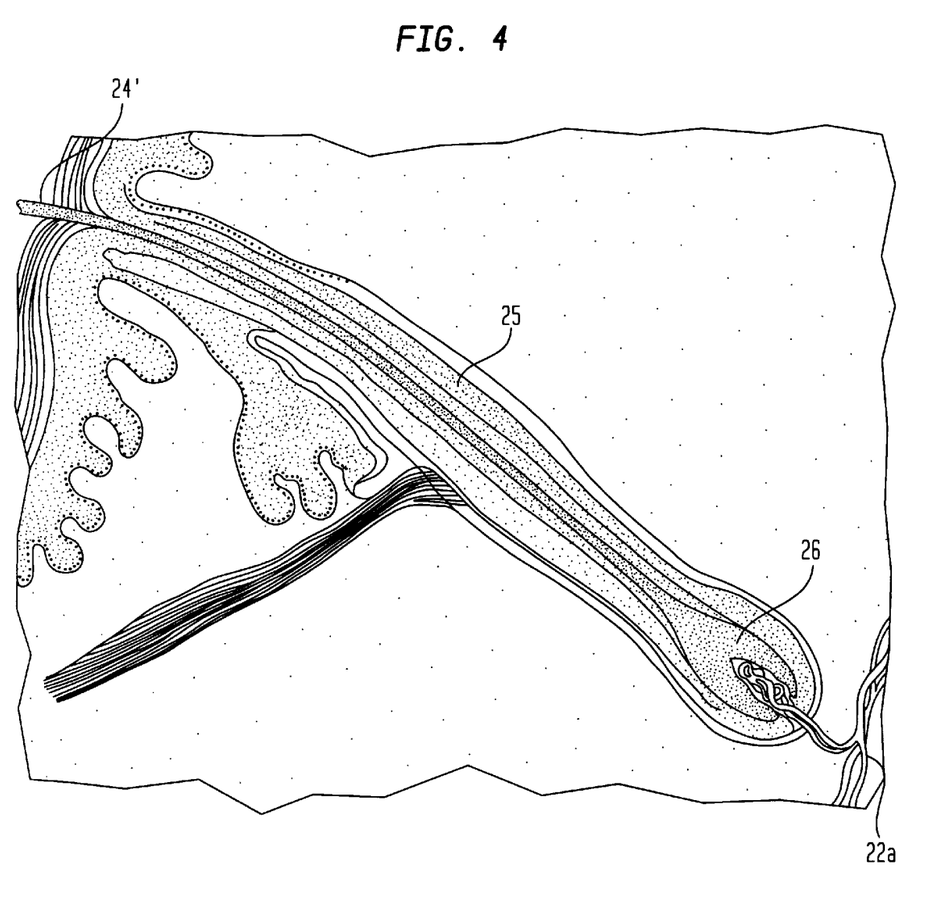
FIG. 4. Depicts a cross-section view of a hair follicle.

FIG. 4 depicts the hair follicle 25 with hair 24 contained therein. Also shown in greater detail is the bulb 26, where cellular division occurs, and manner by which blood flow is supplied 22a to the hair follicle's 25 bulb 26.

Figure 5:
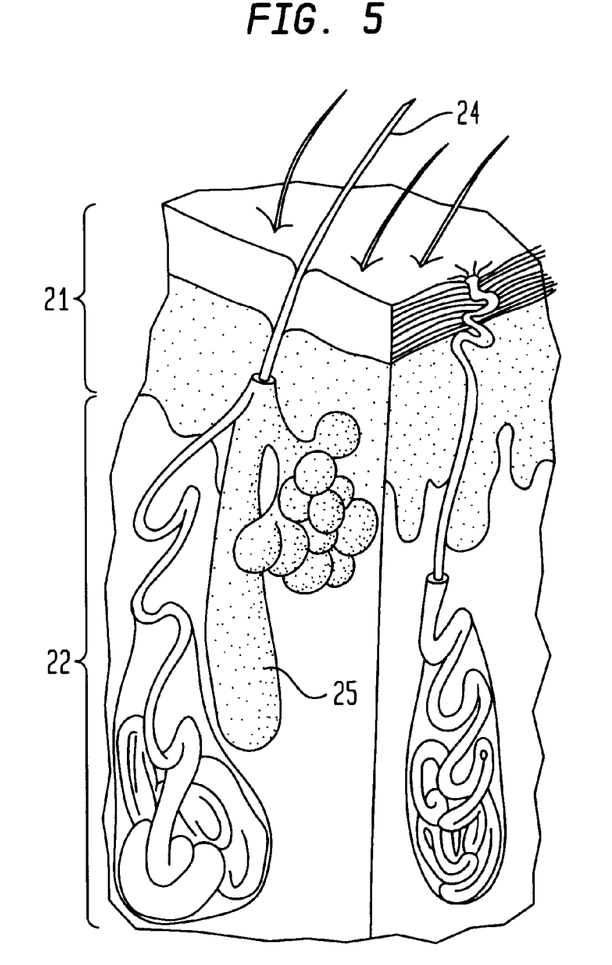
FIG. 5. Depicts a view of a hair follicle.

FIG. 5 depicts a view of a hair follicle 25 evidenced herein is the epidermis 21, dermis 22 and hair shaft 24. The hair shaft is encapsulated in the aforementioned layers 21, 22 in the fair follicle 25. The hair follicle 25 is predominantly located in the dermis 22.

Figure 6:
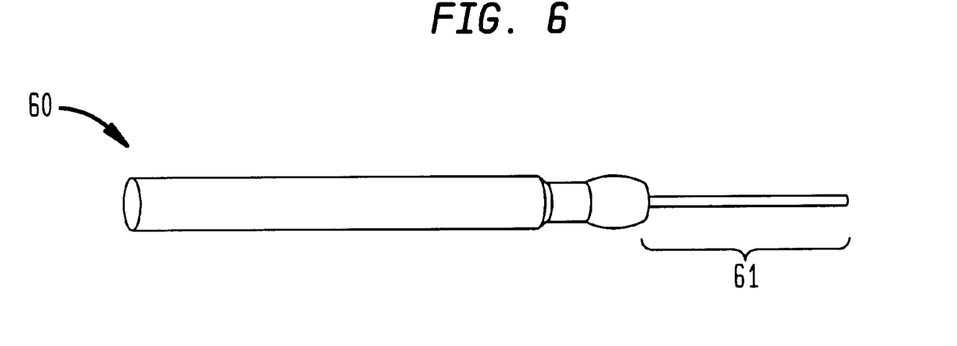
FIG. 6 Depicts a side view of an electrolysis needle/probe.

FIG. 6 depicts a side view of an electrolysis needle/probe 60. Accordingly the tip 61 of the needle/probe 60 is inserted into the follicle of a patient. The needle/probe 60 should be limitedly flexible. Then the needle/probe 60 is "charged" with electrical current after insertion into the follicle of the skin and electrical current maintained for a limited duration. The application of electrical current should be sufficient to coagulate the surrounding cellular structures. The electrical current gently heats and therein coagulates the surrounding cellular structures and thus eliminating the growth of hair.

The diameter of the needle/probe 60 is in direct relation to the diameter of the hair follicle. Accordingly, the needle/probes 60 range in diameter from between 0.003 to 0.006 inches in diameter. In turn, the needle/probes 60 are between 0.0156 and 0.2185 inches in length.

What is taught in this disclosure is a method for low level electrical emissions during epilation that slowly coagulate the cellular structures preventing blood supply and cellular regeneration. This is accomplished, in part, with the teachings in the accompanying Table 1, Table 2, and Table 3, all of which represent patients, their gender and race, past treatment(s), results, needle/probe diameter, depth of insertion, time/duration of insertion, epilator intensity, duration of treatment and results, and the area treated.

Having described the embodiment of the present invention in great detail, it should be apparent that numerous modifications, additions and omissions in the details thereof are possible within the intended spirit and scope of the invention. The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

TABLE 1

| Name | Race | Past Treatment | Needle/Probe (Diameter) | Depth (Inches) | Timing In Sec. | Intensity In watts | Treatment Results By Us | Area |
|---|---|---|---|---|---|---|---|---|
| Gayle L. | White Female | 10 years No Success | .004 | 2/16 | 8 | 1.875 | 3 hrs. 90% done | Chin & lip |
| James M. | White Male | 4 years No Success | .004 | 2/16 | 8 | 1.875 | 2/34 hrs. 95% done | Ears |
| Nina I. | White Female | 10 years 10% success | .003 | 1/32 | 6 | 0.50 | Lip-90% Chin-100% Chest-70% | Lip Chin Chest |
| Teresa N. | White Female | 10 years No Permanency | .003 | 2/16 | 4 | 1.50 | Chin-50% | Chin |
| Linda A. | White Female | No Past Treatment | .004 | 2/16 | 8 | 1.50 | 3 hrs. 90% done | Bikini |
| Maria C. | White Female | 1 year | .003 | 2/16 | 8 | 1.50 | 3 hrs. done | Chin |
| Lucy L. | White Female | 1 year | .004–.003 | 2/16 | 8 | 1.50 | 4 hrs. done | Chin |
| Linda S. | White Female | 3 years | .003 | 1/16 | 5 | 1.00 | 90% | Leg |
| Ilene L. | White Female | 6 years 20% Permanency | .003 | 1/16 | 5 | 1.75 | 90% | Leg |

TABLE 2

| Name | Race | Past Treatment | Needle/Probe (Diameter) | Depth (Inches) | Timing In Sec. | Intensity In watts | Treatment Results By Us | Area |
|---|---|---|---|---|---|---|---|---|
| Gail G. | White Female | No Treatment | .003 | 2/16 | 6 | 1.50 | 4 years done | Chin |
| Pat H. | White Female | 4 years No Success | .003 | 1/16 | 5 | 1.50 | 24–15 min Treatment | Upper Leg |
| Lisa | White Female | None | .004 | 3/16 | 8 | 1.75 | 6 hrs. 70% done | Under Arms |
| Alissa | White Female | 20 hrs. 20% Success | .004 | 2/16 | 6 | 1.00 | 10 hrs. 70% | Chin & Side of Face |
| Wendy H. | White Female | None | .003 | 2/16 | 6 | 1.50 | 20 hrs. | Lip, Chin Feet Abdomen & Breast |
| Paul K. | White Male | None | .003 | 2/16 | 4 | 1.00 | 1½ hrs. 90% done | Center Brow |
| Mary | White Female | 8 years 10% done | .003 | 2/16 | 5 | 1.75 | 24 hrs. 95% done | Lip, Chin & Sides of Face |

TABLE 3

| Name | Race | Past Treatment | Needle/Probe (Diameter) | Depth (Inches) | Timing In Sec. | Intensity In watts | Treatment Results By Us | Area |
|---|---|---|---|---|---|---|---|---|
| Barbara F. | White Female | 40 years ? what was done | .003 | 2/16 | 4 | 1.75 | 20 hrs. done | Entire Face Complete |
| Marie O. | White Female | 7 months 116 hours | .003 | 1/32 to 2/16 | 6 | 0.75 | 50 hrs. 95% done | Face Brow, Breast Feet |
| Eve S. | White Female | 7 years No Success | .003 | 1/16 | 6 | 1.75 | 9 hrs. done | Lip & Chin |
| Pat A. | White Female | 5 years No Success | .003 | 1/16 | 8 | 1.75 | 1 year 80% done | Side of face, lip & chin |
| Sarita M. | White Female | 6 years 10% success | .003 | 2/16 | 6 | 1.875 | 1 year 90% | Lip, Brow, Chin, Breast & Top Leg |

What I claim is:

1. A non-invasive, painless, permanent hair removal process comprising the steps of (a) inserting a flexible probe into an individual hair follicle without perforating the base and the side wall of said follicle;

(b) applying the low-level electrical current through said needle into said follicle for a time period ranges from about 1.0 to about 10.0 seconds to sufficiently cause cell coagulation;

(c) turning off said current;

(d) removing said needle; and (e) removing the hair from said follicle.

2. A process according to claim 1, wherein said probe is inserted into said follicle at a depth which does not penetrate the epidermal or dermal tissue.

3. A process according to claim 2, wherein said depth ranges from about 0.001 to about 0.12 inches.

4. A process according to claim 1, wherein the diameter of said needle is small enough for insertion within an individual hair follicle.

5. A process according the claim 4, wherein the diameter of said needle ranges from about 0.001 to about 0.01 inches.

6. A process according to claim 1, wherein the intensity of said electrical current is sufficient to cause cell coagulation.

7. A process according the claim 6, wherein said current ranges from about 0.1 to about 3.0 watts.

* * * * *